United States Patent [19]

Llopart

[11] 4,318,906
[45] Mar. 9, 1982

[54] MEDICINAL COMPOSITION FOR EXTERNAL USE FOR TREATING WOUNDS

[75] Inventor: Jean-Paul Llopart, Alenya, France

[73] Assignee: Establissement Rinrone, Mauren, Liechtenstein

[21] Appl. No.: 162,313

[22] Filed: Jun. 23, 1980

[30] Foreign Application Priority Data

Jun. 25, 1979 [FR] France .................................. 79 17258

[51] Int. Cl.³ .............................................. A61K 35/78
[52] U.S. Cl. ................................................... 424/195
[58] Field of Search ......................................... 424/195

[56] References Cited

U.S. PATENT DOCUMENTS

1,926,929  9/1933  Abelmann ............................ 424/195
3,068,151  12/1962  Haefele ................................. 424/71

FOREIGN PATENT DOCUMENTS

5975M    4/1968  France .................................. 424/195
2062870  7/1971  France .................................. 424/195

*Primary Examiner*—Donald B. Moyer
*Attorney, Agent, or Firm*—Arnold, White & Durkee

[57] ABSTRACT

A liquid medicinal composition for external use for treating wounds comprises from 450 to 1,000 ml of base tincture of *Centella asiatica*, from 11 to 65 ml of natural essential oil of *Lavandula officinalis*, from 5 to 10 ml of natural essential oil of *Thymus officinalis*, from 5 to 20 ml of natural essential oil of *Rosmarinus officinalis* and from 4 to 14 ml of base tincture of *Aesculus hippocastunum* and preferably also from 0.1 to 6 ml of base tincture of *Medicago sativa*, from 0.1 to 6 ml of base tincture of *Carlina acaulis*, and from 2 to 15 ml of natural essential oil of *Cupressus officinalis*. This composition speeds healing of wounds to a surprising degree.

9 Claims, No Drawings

MEDICINAL COMPOSITION FOR EXTERNAL USE FOR TREATING WOUNDS

The invention relates to a new medicament for external use, which is based on plants and is intended, in particular, for treating wounds.

For treating wounds, the use of solutions of chemical products, such as Mercurochrome or quaternary ammonium salts, has been suggested for a long time. Although widely used, in particular in first interventions, these solutions exhibit the disadvantage of weakening the cell material in which the injury is located, and of being only partially effective.

Antibiotics or sulphamides have also been widely used for the same purpose. Although these products exhibit numerous indisputable advantages, they sometimes have the disadvantage, apart from a certain toxicity and an irritating action at the point of application, exhibited by some of these products, of causing the appearance of a resistant strain of bacteria.

The invention overcomes these disadvantages. It relates to a medicinal composition for external use, which is based on plants, is easy to use and exhibits the advantage of reconstituting the cell material.

This base liquid composition is characterised in that it contains from 450 to 1,000 ml of base tincture of *Centella asiatica*, from 11 to 65 ml of natural essential oil of *Lavandula officinalis*, from 5 to 10 ml of natural essential oil of *Thymus officinalis*, from 5 to 20 ml of natural essential oil of *Rosmarinus officinalis* and from 4 to 14 ml of base tincture of *Aesculus hippocastunum*.

Advantageously, this composition can also contain the following constituent or constituents: from 0.1 to 6 ml of base tincture of *Medicago sativa*, from 0.1 to 6 ml of base tincture of *Carlina acaulis* and from 2 to 15 ml of natural essential oil of *Cupressus officinalis*.

The above designations are those of the Codex, that is to say of the official medical dictionary in France (also referred to as "Pharmacopée" ("Pharmacopee")).

As is known, an "essential oil" is a generally volatile oil obtained by distilling aromatic natural substances of vegetable origin. These oils are widely used in pharmacy and in perfumery.

On the other hand, a "base tincture" results from the maceration of plants, in a pure alcoholic medium, for a practical period of the order of several days. These base tinctures, which are also widely used in pharmacy, are thus at a maximum concentration.

"*Centalla asiatica*" is a plant of the Umbelliferae family; it is sometimes also referred to as hydrocotyle, which is well known for its action of controlled cytophylactic regeneration. Preferably, this macerate is prepared in alcohol at a temperature of at least 80° C. and for an appreciable period which is longer than the customary maceration periods for the current Codex hydrocotyle tinctures.

The use of this plant as a cicatrisant medicament for external use has been known for a very long time (see, for example, Special French Patent for Medicaments BSM 4209 M). Its main therapeutic active principle is the triterpene extract.

"Lavandula", which, as is known, is referred to as lavender, is a plant of the Labiatae family. The main constituents of essential oil of lavender are linalyl and geranyl ethers, geranio-linalol, cineol, d-borneal, limonene, l-pinene, caryophyllene, butyric and valeric acid esters, coumarin, terpenes, terpene alcohols and, in particular, linalol esters (acetate) and geraniol esters. This essential oil is known for its antiseptic and cicatrisant action when used externally.

"Thymus", which is commonly referred to as thyme, is also a plant of the Labiatae family and the main constituents of its essential oil are oils (phenols) of thymol, carvacrol, cymol, borneol, linalol and tannin, paracymene and terpene derivatives, terpinenes and a small amount of cyneol. This oil is well known for its antiseptic, bactericidal and antiputrefactive action when used externally.

"Rosmarinus", which is commonly referred to as rosemary, is also a plant of the Labiatae family and the main constituents of its essential oil are essential oils of pipene, camphene, cineol, borneol, camphors and bornyl acetate. This oil has an antiseptic and cicatrisant, resolvent external action.

"*Aesculus hippocastunum*", which is commonly referred to as horse-chestnut, is a plant of the Hippocastanaceae family and its base tincture, which is formed from the seed and the seed coat, contains, an essential active principles, triterpene saponins, including esculin in particular, and flavonic acid derivatives of quercetin and of kaempferol, and catechuic tannins, and the main constituents thereof are saponins, tannins, a glucoside and flavones. This tincture is well known as a blood activator and for its anti-inflammatory properties.

"*Medicago sativa*", which is commonly referred to as lucerne, is a plant of the Leguminosae family and the main constituents of its base tincture are a provitamin A (beta-carotene), vitamins C, D and $K_1$ and inorganic salts of calcium, potassium, iron and phosphorus. This tincture has a recalcifying and antihaemorrhagic action.

"*Carlina acaulis*", which is commonly referred to as carline thistle, is a plant of the Compositae family and the main constituents of its base tincture are essential oils: acetylene derivatives (carline oxide: furylbenzylacetylene). This tincture has a reconstituting, antidermatosic, tonic and antibiotic action and is used an activator of the sympathetic nervous system.

"*Cupressus*" is a plant of the Coniferae family. The essential constituents of the essential oil of Cupressus, the latter commonly being referred to as cypress, are tannins, and essential oils: d-pinene, d-campene, d-sylvestene, cymene, a ketone, sabinol, a terpene alcohol, valeric acid and cypress camphor. This essential oil has a direct phlebotomic vascular action, that is to say a vasoconstrictive and tonic action on the veins.

Each of the above essential oils and base tinctures are already well known for their pharmaceutical applications. The preparation of the composition according to the invention consists in bringing these constituents together in determined and precise proportions and in determined and precise forms, and this causes a synergy and a reaction between them. The final base composition obtained gives effects and results which are considerably improved in comparison with the effects and results obtained with each constituent taken in isolation and successively or in a cumulative manner, and this is unexpected and surprising.

It has been determined that the best results are obtained with a base composition containing 986 ml of base tincture of hydrocotyle, 65 ml of essential oil of lavender, 10 ml of essential oil of thyme, 17 ml of essential oil of rosemary, 14 ml of base tincture of horse-chestnut and, advantageously, 1.7 ml of base tincture of lucerne, 1.5 ml of base tincture of carline and 9 ml of essential oil of cypress.

The addition of these last three constituents improves the activity of the active principles, in particular as a consequence of the specific orientation of each of them.

This base composition is in the form of a deep green-coloured liquid tincture. Most generally, it can be used as such, that is to say at maximum concentration. However, for certain applications which do not require optimum activity, this composition can be diluted, for example in alcohol. For example, one liter of this base composition can be diluted in 300 cm³ of ethanol.

To prepare this composition, the essential oils or the base tinctures of each of the constituents are prepared in a known manner. At ambient temperature, all the tinctures and all the essential oils are mixed separately, whilst stirring, and finally, still at ambient temperature, the whole is mixed, whilst stirring, the essential oils being incorporated into the tinctures.

In practice, the liquid compositions for treating wounds, according to the invention, can be used in a known manner, for example by application on compresses. Advantageously, however, this composition is used by spraying directly onto the wound.

The pharmacological properties of these compositions are essentially cicatrisant and antiseptic properties.

Furthermore, these compositions have been tested for acute toxicity by oral administration to rats and mice, and the 50% lethal doses are as follows:

| rats | male | 11.41 g |
|---|---|---|
| | female | 11.59 g |
| mice | male | 11.29 g |
| | female | 11.89 g |

It can thus be deduced that these compositions have a very low toxicity.

In terms of therapeutic application to animals or humans, there may be mentioned the cicatrisation and disinfection of open wounds of various origins, atonic wounds of various origins, varicose ulcers, scabs, mycosis and dermatosis.

It is also possible to mention wounds of any kind caused by injury or burning, scabs and leg ulcers, which arise either in the case of persons previously suffering from phlebitis, or in the case of persons suffering from varicosis. As regards wounds caused by injury, experiment has demonstrated that the speed of cicatrisation of wounds treated with the compositions according to the invention is virtually twice that of wounds treated by other processes, in particular with antibiotics or other conventional medications.

By way of indication, it has been determined that the average posology is 1 to 6 cm³ per day, it being understood that this posology can be increased if there is resistance.

The manner in which the invention can be put into effect and the advantages which result therefrom will become more clearly apparent from the following illustrative embodiments which are given by way of indication and without implying a limitation.

EXAMPLE 1

In a known manner, either a base tincture or an essential oil of each of the constituents of the base composition in alcohol is prepared, depending on the particular case.

At ambient temperature (20° C.), the following are mixed in order, whilst stirring: 986 ml of base tincture of *Centella asiatica* (hydrocotyle), 14 ml of base tincture of *Aesculus hippocastunum* (horse-chestnut), 1.5 ml of base tincture of *Carlina acaulis* (carline thistle) and 1.7 ml of base tincture of *Medicago sativa* (lucerne).

Independently and still at ambient temperature (20° C.), the following are also mixed in order, whilst stirring: 65 ml of natural essential oil of *Lavandula officinalis* (lavender), 17 ml of natural essential oil of *Rosamarinus officinalis* (rosemary), 10 ml of natural essential oil of *Thymus officinalis* (thyme) and 9 ml of natural essential oil of *Cupressus officinalis* (cypress).

The mixture of base tincture and the mixture of essential oils are then mixed, still at ambient temperature and whilst stirring, the mixture of oils being poured into the mixture of tinctures.

This gives 1,104.2 ml of a deep green-coloured liquid composition having an alcoholic strength of 92°.

Using a spray gun (average spraying of about 1 cm³), this composition is projected onto an external varicose ulcer with atony, on a normal human subject, at a rate of 4 to 6 sprayings per day.

After fourteen days, the wound closes up and has perfectly healed after forty days of treatment. By By way of comparison, current treatments with antibiotics, sulphamides or corticoids frequently take several months and give sometimes random results.

EXAMPLE 2

An open wound caused by injury in the flesh, on a sample of graded healthy rats, is treated with the composition of Example 1 at a rate of 3 to 4 sprayings per day.

Depending on the size of the wounds (width, depth), they have closed up after two to four days and this considerably reduces the risk of infection.

On the other hand, by way of comparison, treatment of the same injuries on a comparable sample of the same subjects would have required injections of antibiotics and would have shown a retarded change in the cells, which very frequently causes the putrefaction of the flesh.

EXAMPLE 3

A scab on a bed-ridden human subject is treated with the same composition as in Example 1 at a rate of six sprayings per day.

After fifteen days of treatment, it is found that the putrid elements have disappeared, and after twenty days, the scan can be considered as healed.

This is all the more unexpected because the currently used methods do not make it possible suitably to treat wounds of this kind, which in practice close up with great difficulty.

EXAMPLE 4

The composition of Example 1, at different concentrations in 90° strength ethanol, is used to treat various wounds at a rate of two to five sprayings per days. The results have been grouped in the following table on page 12.

As already stated, the cicatrisant action of *Centalla asiatica* has been known for a very long time. However, this action is too frequently rapid, with the result that, in the case of deep wounds, cicatrisation can sometimes take place on the surface whereas the centre of infection still remains inside. On the other hand, by virtue of the synergy of this preponderant compound with the other compounds, the composition according to the invention results in a controlled cicatrisant action with cell regeneration, without a subcutaneous centre of infection.

In other words, the combination of the various constituents makes it possible at one and the same time to have a better cicatrisant action and to combat infection and inflammation without detracting from the other properties. Thus, the synergy of the various constituents (tinctures and essential oils) not only exhibits the advantages known for each of these constituents, but, in particular, improves and strengthens the particular action of each constituent, without detracting from the other properties; this demonstrates interaction and was totally unexpected.

of base tincture of *Centella asiatica*, about 65 ml of essential oil of *Lavandula officinalis*, about 10 ml of essential oil of *Thymus officinalis*, about 17 ml of essential oil of *Rosamarinus officinalis* and about 14 ml of base tincture of *Aesculus hippocastunum*.

7. Composition according to claim 6, which also contains about 1.7 ml of base tincture of *Medicago sativa*, about 1.5 ml of base tincture of *Carlina acaulis* and about 9 ml of essential oil of *Cupressus officinalis*.

8. Liquid medicinal composition diluted in ethanol for external use for treating wounds comprising:
from 450 to 1,000 ml of base tincture of *Centella asiatica*;

| Dose of the composition in 90° strength alcohol | Cutaneous injury | 2nd degree burn | Atonic wound | Varicose ulcer | Scab |
|---|---|---|---|---|---|
| 3% | Wound heals after 8 days | Does not tend to become infected | Does not tend to become infected | NONE | NONE |
| 7% | Wound heals after 7 days | Does not tend to become infected | Does not tend to become infected | NONE | NONE |
| 15% | 6 DAYS | Slow cell regeneration | Start of cicatrisation | Purulent greenish-gray layer starts to peel off | More pronounced deodorisation |
| 25% | 5 DAYS | Rapidly delimits healthy and diseased tissues | Gradual cicatrisation, deodorant action | Appearance of granulation tissues | More pronounced deodorisation |
| 50% | 5 DAYS | Rapid regeneration | The wound fills up | The wound has a very good appearance | Distinct delimitation of the necrotic edges |
| 75% | 4 DAYS | Cicatrised | Wound almost closed up | Granulating fundus | Progressive regeneration, the flesh reforms |
| 100% | 48 HOURS | Cicatrised after 6 days | Cicatrised | Wound almost closed up | Very advanced cicatrisation |

We claim:

1. Liquid medicinal composition for external use for treating wounds comprising from 450 to 1,000 ml of base tincture of *Centella asiatica*, from 11 to 65 ml of natural essential oil of *Lavandula officinalis*, from 5 to 10 ml of natural essential oil of *Thymus officinalis*, from 5 to 20 ml of natural essential oil of *Rosmarinus officinalis* and from 4 to 14 ml of base tincture of *Aesculus hippocastunum*.

2. Composition according to claim 1, which also contains from 0.1 to 6 ml of base tincture of *Medicago sativa*.

3. Composition according to claim 1, which also contains from 0.1 to 6 ml of base tincture of *Carlina acaulis*.

4. Composition according to claim 1, which also contains from 2 to 15 ml of natural essential oil of *Cupressus officinalis*.

5. Composition according to claim 1, which also contains from 0.1 to 6 ml of base tincture of *Medicago sativa*, from 0.1 to 6 ml of base tincture of *Carlina acaulis*, and from 2 to 15 ml of natural essential oil of *Cupressus officinalis*.

6. Composition according to claim 1 or claim 5, which is diluted in ethanol and comprises about 986 ml of base tincture of *Centella asiatica*, about 65 ml of essential oil of *Lavandula officinalis*, about 10 ml of essential oil of *Thymus officinalis*, about 17 ml of essential oil of *Rosamarinus officinalis* and about 14 ml of base tincture of *Aesculus hippocastunum*.

7. Composition according to claim 6, which also contains about 1.7 ml of base tincture of *Medicago sativa*, about 1.5 ml of base tincture of *Carlina acaulis* and about 9 ml of essential oil of *Cupressus officinalis*.

8. Liquid medicinal composition diluted in ethanol for external use for treating wounds comprising:
from 450 to 1,000 ml of base tincture of *Centella asiatica*;
from 11 to 65 ml of natural essential oil of *Lavandula officinalis*;
from 5 to 10 ml of natural essential oil of *Thymus officinalis*;
from 5 to 20 ml of natural essential oil of *Rosmarinus officinalis*;
from 2 to 15 ml of natural essential oil of *Cupressus officinalis*;
from 4 to 14 ml of base tincture of *Aesculus hippocastunum*;
from 0.1 to 6 ml of base tincture of *Medicago sativa*; and
from 0.1 to 6 ml of base tincture of *Carlina acaulis*.

9. Liquid medicinal composition diluted in ethanol for external use for treating wounds comprising:
about 986 ml of base tincture of *Centella asiatica*;
about 65 ml of essential oil of *Lavandula officilinas*;
about 10 ml of essential oil of *Thymus officinalis*;
about 17 ml of essential oil of *Rosmarinus officinalis*;
about 14 ml of base tincture of *Aesculus hippocastunum*;
about 1.7 ml of base tincture of *Medicago sativa*;
about 1.5 ml of base tincture of *Carlina acaulis*; and
about 9 ml of essential oil of *Cupressus officinalis*.

* * * * *